United States Patent [19]

Grego

[11] Patent Number: 4,565,449

[45] Date of Patent: Jan. 21, 1986

[54] METHOD OF AND APPARATUS FOR DETERMINING REFRACTIVE-INDEX PROFILES OF CYLINDRICAL TRANSPARENT BODIES

[75] Inventor: Giorgio Grego, Turin, Italy

[73] Assignee: Cselt Centro Studi e Laboratori Telecomunicazioni S.p.A., Turin, Italy

[21] Appl. No.: 465,014

[22] Filed: Feb. 8, 1983

[30] Foreign Application Priority Data

Feb. 10, 1982 [IT] Italy .............................. 67150 A/82

[51] Int. Cl.$^4$ .............................................. G01B 9/02
[52] U.S. Cl. ................................... 356/361; 356/73.1; 356/349
[58] Field of Search ....................... 356/73.1, 349, 361

[56] References Cited

U.S. PATENT DOCUMENTS 3,463,924 8/1969 Culshaw et al. ................. 356/349 X
3,881,823 5/1975 De Lang et al. .

OTHER PUBLICATIONS

Koronkevich et al., "Interference Microscope with a Frequency Shift for the Investigation of the Refractive-Index Profiles of Glass Fibers", *Sov. J. Quant. Elec.*, vol. 9, No. 10, p. 1332, Oct. 1929.
Sommargen, "Optical Meterodyne Profilometry", *Applied Optics*, vol. 20, No. 4, pp. 610-618, Feb. 1981.
Dietrich Marcuse, Herman M. Presby; Index Profile Measurements of Fibers and Their Evaluation; Proceedings of the IEEE, vol. 68, No. 6, Jun. 1980.
Article entitled "Principles of Optical Fiber Measurements", by Dietrich Marcuse, pp. 150-159.
Article entitled "P 101 Preform Analyser".

*Primary Examiner*—Davis L. Willis
*Assistant Examiner*—Matthew W. Koren
*Attorney, Agent, or Firm*—Karl F. Ross; Herbert Dubno

[57] ABSTRACT

A body transparent to laser radiation, such as an optical fiber or a preform thereof, is transluminated by a monochromatic beam of a frequency in the THz range split off from a composite laser beam with two closely spaced frequencies produced by the Zeeman effect; the width of that beam in a plane transverse to the body axis is at least equal to the diameter of that body. Another monochromatic beam at the second laser frequency bypasses the transparent body and is recombined with the first beam downstream of the transluminated body to form a field of radiation which is photoelectrically sampled at closely spaced locations in the aforementioned transverse plane to provide a multiplicity of electrtical signals in the MHz range differing in phase from a reference wave of the same frequency photoelectrically obtained from the same monochromatic beams. The phase differences, determined by a comparator, are fed to a calculator computing the refractive-index profile therefrom.

13 Claims, 3 Drawing Figures

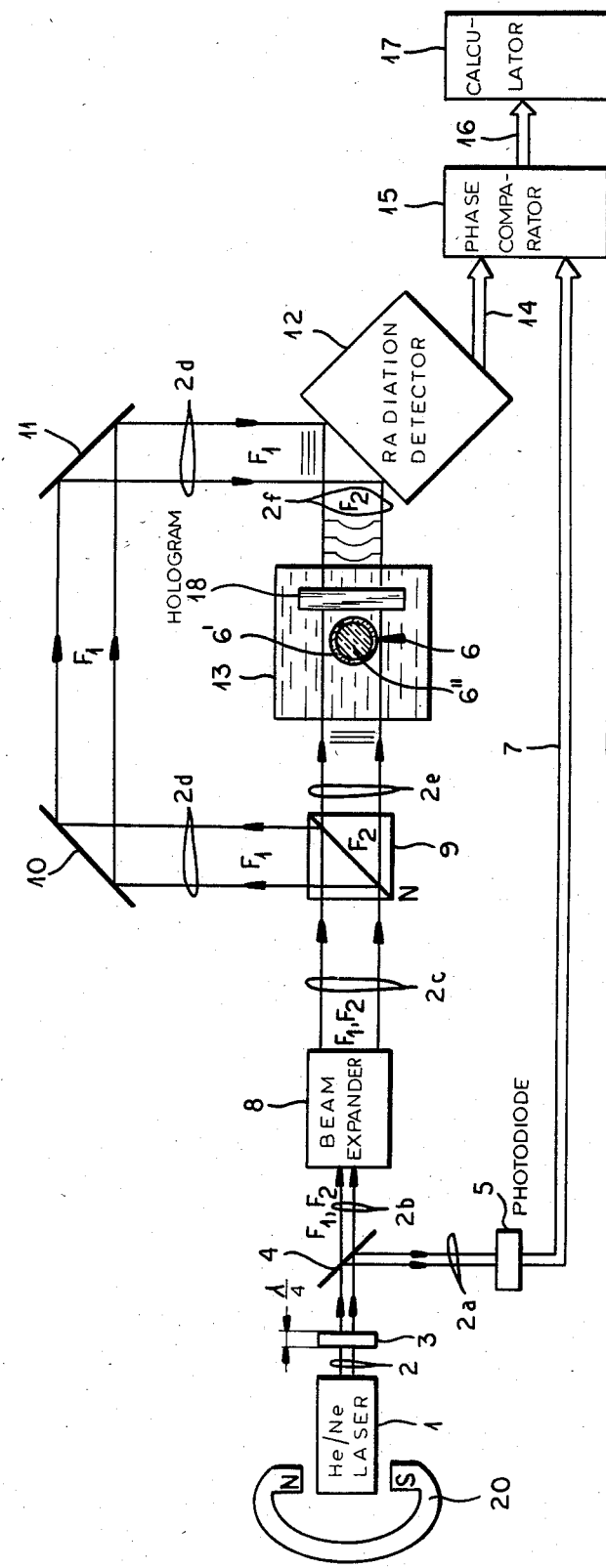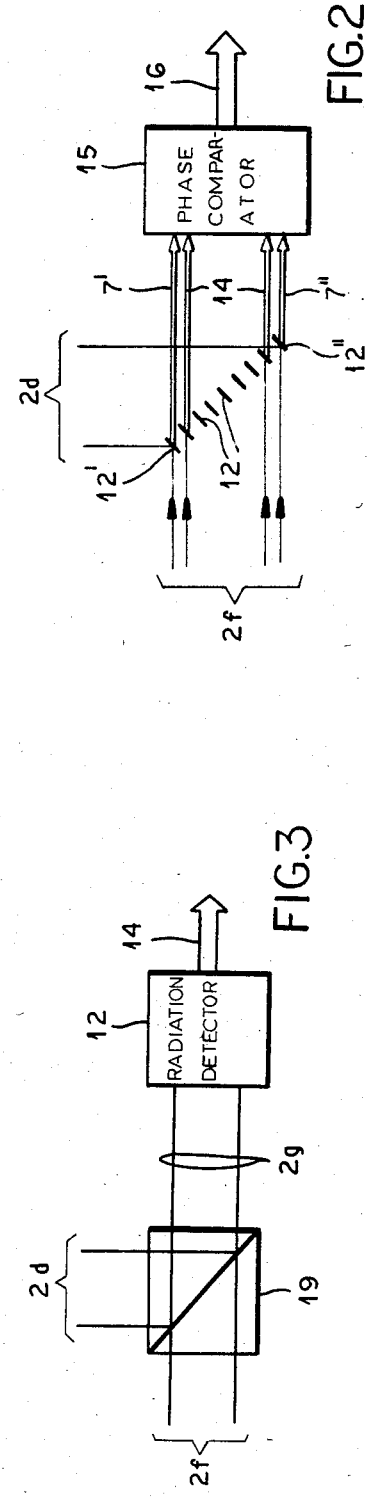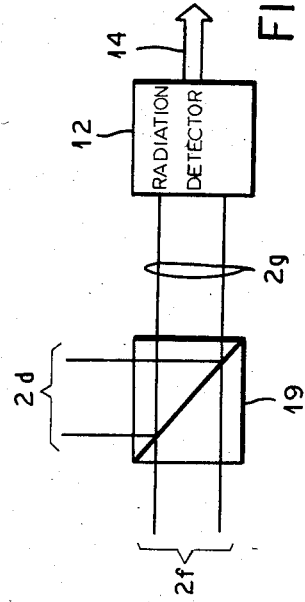

METHOD OF AND APPARATUS FOR DETERMINING REFRACTIVE-INDEX PROFILES OF CYLINDRICAL TRANSPARENT BODIES

FIELD OF THE INVENTION

My present invention relates to a method of determining the refractive-index profile of a cylindrical transparent body, such as an optical fiber or a preform used in its manufacture, as well as to an apparatus for carrying out this method.

BACKGROUND OF THE INVENTION

The refractive-index profile of an optical fiber essentially determines its significant transmission characteristics such as light-collection efficiency, bandwidth and containment of luminous energy. If the index profile can be ascertained during manufacture of a fiber, as by means of measurements made on a preform, departures from prescribed values can be readily corrected. Naturally, such ascertainment would have to be carried out in a nondestructive manner to preserve the continuity of the manufacturing process.

In a paper presented at the Sixth European Conference on Optical Communications, held Sept. 16-19, 1980 at York, England, an apparatus for such nondestructive measurement of the refractive-index profile of an optical-fiber preform has been described by I. Sasaki, D. N. Payne, R. J. Mansfield and M. J. Adams of the Department of Electronics of Southampton University, Southampton, England. Such an apparatus, which is now commercially available under the designation P101 Preform Analyzer, utilizes a monochromatic beam of parallel light rays transluminating a preform in a plane transverse to its axis. The beam and the preform are relatively shifted within that plane in a succession of steps and the transluminating rays are focused in each position by a spherical lens onto a photodetector after traversing a rotating chopper which correlates the ray path with a predetermined reference position to determine the angle of refraction undergone by the beam. This known system, however, is rather complex and consequently expensive on account of its movable parts and the necessary synchronization between their motion and the instants of measurement.

OBJECTS OF THE INVENTION

An important object of my present invention, therefore, is to provide a simpler method of determining the refractive-index profile of a test object—such as an optical fiber or an associated preform—in a nondestructive manner.

A related object is to provide a relatively simple apparatus for implementing this method.

SUMMARY OF THE INVENTION

In accordance with my present invention, the refractive-index profile of a generally cylindrical test object or workpiece transparent to luminous radiation is determined by the steps of (a) generating a first and a second monochromatic beam of luminous radiations of constant frequencies differing slightly from each other, (b) deriving from these beams an electrical reference wave of a beat frequency corresponding to the difference between the beam frequencies, (c) transluminating the test object over its entire width with parallel rays of the second beam in a plane transverse to the object axis, (d) mixing the transluminating rays of this second beam with rays of the first beam (which avoid the test object) in a field of radiation within the aforementioned transverse plane, that field lying downstream of the test object and extending over its entire width, (e) photoelectrically sampling the field of radiation at a multiplicity of closely spaced locations to produce respective electrical signals of the same beat frequency as the reference wave but differing therefrom in phase to an extent dependent on the refractive index of the parts of the test object traversed by the respective transluminating rays, (f) determining the phase differences between these electrical signals and the reference wave at each such location, and (g) computing the refractive-index profile of the test object from the detected phase differences.

Advantageously, pursuant to a more particular feature of my invention, the two monochromatic beams are obtained from a composite beam emitted by a common source, specifically a laser subjected to a magnetic field which causes the well-known Zeeman effect. The two constituent radiations of such a composite beam are circularly polarized, with opposite senses of rotation, at the laser output and can be readily separated from each other by such conventional means as a quarter-wave plate followed by a polarizer.

In a commonly owned application of even date, filed by me jointly with Gianni Coppa under Ser. No. 465,014, the use of such a Zeeman-effect laser for measuring the thickness and the refractive index of a transparent body has been disclosed. As mentioned there, the phase shift undergone by radiation in the THz range—such as a laser beam—traversing an optical fiber or preform cannot be directly measured with equipment currently available; such a phase shift is readily measurable, however, in an electrical wave whose frequency lies in the low MHz range, specifically one that corresponds to the difference between two closely adjoining laser frequencies separated by preferably a few MHz. The reference wave is generated by first photoelectric means positioned to receive rays from both monochromatic beams, e.g. via a beam splitter disposed upstream of the polarizer which is used to separate the laser frequencies. An optical system, including the aforementioned beam-separating means, guides rays of the first beam around the test object and guides parallel rays of the second beam through that test object in the transverse plane referred to, the two sets of rays being combined in the downstream field of radiation where they are intercepted by second photoelectric means deriving therefrom the multiplicity of individually phase-shifted electrical signals to be compared with the reference wave. The first photoelectric means could also be disposed in this field of radiation to intercept rays of the first beam along with rays of the second beam bypassing the test object in the transverse plane. In the latter instance, the two photoelectric means may be part of a single radiation detector such as, for example, a television camera.

An algorithm to be used in the computation of the refractive-index profile is expressed by the relationship $$n(\rho) - n_c = -\frac{\lambda}{2\pi^2} \cdot \int_\rho^\mathcal{R} \frac{d\phi}{dr} \cdot \frac{dr}{\sqrt{r^2 - \rho^2}}$$

derived from formulas for interferometric measurements given on pages 150-159 of a book entitled "Principles of Optical Fiber Measurements" by Dietrich Marcuse, published 1981 by Academic Press. In this equation, $n(\rho)$ is the refractive index of the core of an optical fiber or preform at a point spaced by a distance $\rho$ from the axis, it being assumed that this index is uniform throughout an annular zone of the same radius $\rho$. Radius $r > \rho$ represents the distance of a transluminating ray from the axis, with $d\phi/dr$ representing the phase gradient within the translumination plane as determined by the phase difference between the ray considered and its neighbors intercepted at adjacent locations. The parameter $\lambda$ denotes the wavelength of the second beam. The constant refractive index of the cladding surrounding the core is given by $n_c$.

When the rays of the two beams mixed in the radiating field downstream of the test object are intercepted by photoelectric means in the form of discrete detectors such as photodiodes, the integral in the foregoing equation is only approximated by a finite sum. In practice, this also applies to the case of a television camera whose output signal is sampled during a sweep at discrete intervals in order to be usable by a digitally operating calculator or computer. The upper limit of $\infty$ could be replaced by the core radius R since $D\phi/dr$ is zero beyond that radius.

Pursuant to another feature of my invention, the phase shifts undergone by the transluminating rays may be compensated in whole or in part by a transparent element juxtaposed with the workpiece in the path of the second beam, this element having a refractive-index profile which is the complement of a known profile such as that of a standard fiber or preform to be duplicated. In that case, the residual phase shifts fed to the calculator represent deviations from the standard profile which can be rectified in the manufacturing process.

BRIEF DESCRIPTION OF THE DRAWING

The above and other features of my invention will now be described in detail with reference to the accompanying drawing in which:

FIG. 1 is a diagrammatic view of an apparatus for the determination of a refractive-index profile in accordance with my invention; and FIGS. 2 and 3 illustrate partial modifications of the apparatus of FIG. 1.

SPECIFIC DESCRIPTION

In the drawing, single lines are used for ray paths whereas double-line arrows denote electrical connections.

As shown in FIG. 1, a laser 1 of the He/Ne type is disposed in the field of a permanent magnet 20 in order to emit a composite beam 2 consisting of two monchromatic radiations of frequencies $F_1$ and $F_2$ generated by the Zeeman effect. The two radiations, which are circularly polarized with opposite senses of rotation, lie in the THz range and differ from each other by a beat frequency of about 2 MHz. Typically, the order of magnitude of these two laser frequencies is 275 THz.

A quarter-wave plate 3 converts the circular polarization of frequencies $F_1$ and $F_2$ into linear polarization in two orthogonal planes. These radiations are partly deflected by a beam splitter 4 onto a photodiode 5 over a path indicated at $2a$; the beam splitter 4 could also be interposed between the laser output and plate 3. Photodiode 5 delivers an electrical reference wave of frequency $|F_1 - F_2|$ on a lead 7 to an input of a phase comparator 15. The remainder $2b$ of the composite beam arrives at a beam expander 8 which broadens it into an enlarged bundle $2c$ of parallel rays whose width in the plane of the drawing, i.e. in a plane transverse to the axis of a cylindrical test object 6 to be transluminated, equals or preferably exceeds the diameter of that test object. The latter is a preform as used in the manufacture of optical fibers, having a cladding $6'$ of constant refractive index $n_c$ and a core $6''$ whose refractive index $n(\rho)$ varies with distance $\rho$ from its axis. Preform 6 is held in a transparent cell 13 which is filled with a liquid matching the refractive index $n_c$ of the cladding.

Before reaching the cell 13, the broadened beam $2c$ traverses a polarizer 9 which separates its constituent frequencies $F_1$ and $F_2$ from each other. A monochromatic beam $2d$ of frequency $F_1$ is deflected onto a path bypassing the cell 13, this path being defined by optical means including a pair of mirrors 10 and 11. Another monochromatic beam of frequency $F_2$ traverses the polarizer 9 as well as the cell 13 so that most of its rays transluminate the workpiece 6. Owing to its nonuniform index $n(\rho)$, the rays passing through the core in the transverse plane are refracted to produce distorted wavefronts in an outgoing part $2f$ of beam $2e$. In the field of radiation of beam $2f$ its rays are recombined with those of beam $2d$ reflected by mirror 11; the merging rays are intercepted by a radiation detector 12. The interaction of the two sets of rays of slightly different laser frequencies produces a multiplicity of electrical signals in an output connection 14 of radiation detector 12 extending to a set of further inputs of phase comparator 15. The latter detects the phase differences between the output signals of detector 12 and the reference wave present on lead 7, feeding that information by way of a connection 16 to a calculator 17 for computation of the refractive-index profile of preform core $6''$.

When the receiving surface of photodetector 12 is defined by an array of closely spaced photodiodes, connection 14 is a wire multiple on which their output signals appear simultaneously. Alternatively, this receiving surface could be the photocathode of a television camera, in which case the differently phase-shifted electrical signals are initially indistinguishable from one another and are individualized only by repetitive sampling of the output voltage generated in the course of a scan; this sampling may be carried out in the detector 12 or in phase comparator 15. In any event, calculator 17 receives a multiplicity of phase-difference values from which the phase gradient $d\phi/dr$ can be derived in order to yield the desired refractive-index profile in terms of the difference $n(\rho) - n_c$ according to the formula given above. Successively obtained samples or their phase differences will have to be stored in unit 12, 15 or 17 for evaluation.

As further shown in FIG. 1, a phase-shift compensator 18 may be juxtaposed with the preform 6 inside cell 13 for concurrent translumination by the rays traversing the core $6''$. Element 18 advantageously is a complementary hologram of a standard workpiece; the refractive-index differences computed by calculator 17 represent then only the departures of the preform profile from the standard.

The information fed to calculator 17 need not be limited to phase differences detected in a single transverse plane. With a photodiode array in the form of an orthogonal matrix, or with successive line scans in the case of a TV camera, different cross-sections of the preform can be explored at the same time.

It may be pointed out that the ray paths established by the mirrors 10 and 11 of FIG. 1 differ in length among one another so as to introduce additional phase shifts which would have to taken into account by the calculator 17 unless they are compensated by additional optical means in the trajectory of beam 2d. Such additional phase shifts can be avoided if, as shown in FIG. 2, the receiving surface of the radiation detector is inverted by a staggering of photodiodes 12 in the opposite direction. FIG. 2 further shows that the outermost rays of beam 2e, bypassing the test object 6, can be mixed with corresponding rays of beam 2d and intercepted by photodiodes 12', 12" to provide electrical reference waves delivered to phase comparator 15 via leads 7' and 7"; normally, one such reference wave would suffice. This arrangement eliminates the need for the beam splitter 4, the photodiode 5 and the connection 7 of FIG. 1.

FIG. 3 illustrates another way of eliminating the path-length differences of beam 2d. In this case the beams 2f and 2d are recombined with the aid of a second polarizer 19 to yield a composite beam 2g impinging upon radiation detector 12 whose receiving surface is now perpendicular to the path of beam 2f. Naturally, the apparatus of FIG. 3 could also utilize preform-bypassing rays of beams 2e and 2f for generating a reference wave as described in connection with FIG. 2.

I claim:

1. A method of determining the refractive-index profile of a generally cylindrical test object transparent to luminous radiation, the refractive index of said test object being constant at a given distance $\rho$ from the axis thereof, comprising the steps of:
   (a) generating a first and a second monochromatic beam of luminous radiations of constant frequencies differing slightly from each other;
   (b) deriving from said first and second beams an electrical reference wave of a beat frequency corresponding to the difference between the beam frequencies;
   (c) transluminating the test object over the entire width thereof with parallel rays of said second beam in a plane transverse to the axis of said test object;
   (d) mixing the transluminating rays of said second beam with rays of said first beam, avoiding the test object, in a field of radiation within said plane which lies downstream of the test object and extends over the entire width thereof;
   (e) photoelectrically sampling said field of radiation at a multiplicity of closely spaced locations to produce respective electrical signals of the same beat frequency as said reference wave but differing in phase therefrom to an extent dependent on the refractive index of the parts of the test object traversed by the respective transluminating rays;
   (f) determining the phase differences between said signals and said reference wave at said locations;
   (g) computing the refractive-index profile of the test object from said phase differences; and
   (h) interposing a phase-shift compensator of known refractive-index profile in the path of said transluminating rays whereby the profile computed in step (g) represents deviations from the complement of the known profile of said compensator.

2. A method of defined in claim 1 wherein the test object is a vitreous body with a cladding of constant refractive index $n_c$ surrounding a core whose refractive index $n(\rho)$ varies with distance $\rho$, the calculation in step (g) being performed on the refractive-index profile of the core according to the relationship $$n(\rho) - n_c = -\frac{\lambda}{2\pi^2} \int_\rho^\infty \frac{d\phi}{dr} \cdot \frac{dr}{\sqrt{r^2 - \rho^2}}$$

where $\phi$ is the phase of a transluminating ray traversing said core at a distance $r > \rho$ from the axis and $\lambda$ is the wavelength of said second beam.

3. A method as defined in claim 1 wherein said first and second monochromatic beams are obtained from a composite beam emitted by a common source.

4. A method as defined in claim 3 wherein said source is a laser subjected to a magnetic field causing a Zeeman effect.

5. A method as defined in claim 4 wherein the frequencies of said first and second beams lie in the THz range and are separated from each other by a difference of a few MHz.

6. A method as defined in claim 3 wherein said reference wave is obtained in step (b) by photoelectrically mixing rays from said source ahead of a point upstream of the test object at which the monochromatic constituents of said composite beam are separated into rays of the frequency of said second beam transluminating the test object and rays of the frequency of said first beam avoiding the test object.

7. A method as defined in claim 1 wherein the composite beam emitted by said source is broadened in said plane to more than the diameter of the test object whereby certain rays of said second beam bypass the test object, the bypassing rays being photoelectrically mixed downstream of the test object with rays from said first beam in step (b) to provide said reference wave.

8. A method as defined in claim 1 wherein the test object is a workpiece involved in the process of producing an optical fiber, said compensator being a complementary hologram of a standard workpiece to be duplicated.

9. An apparatus for determining refractive-index profile of a generally cylindrical test object transparent to luminous radiation with a refractive index which is constant at a given distance from the axis thereof, comprising:
   a holder for the test object to be examined;
   a source of monochromatic first and second beams of luminous radiation of constant frequencies differing slightly from each other;
   first photoelectric means positioned to receive rays from said first and second beams to derive therefrom an electrical reference wave of a beat frequency corresponding to the difference between the beam frequencies;
   optical means for guiding rays of said first and second beam around said test object and for guided parallel rays from said second beam through said test object in a plane transverse through the axis thereof for combination with the rays of said first beam in a field of radiation downstream of said test object extending over the entire width of the latter;
   second photoelectric beams disposed in said field at a multiplicity of closely spaced location for intercepting rays from both beams and deriving therefrom a multiplicity of electrical signals of the same beat frequency as said reference wave but differing in phase therefrom at said locations to an extent depending on the refractive index of the parts of said test object traverse by the rays of said second beam respectively arriving thereat;

phase comparison means is connected to said first and second photoelectric means for determining the phase differences between said electrical signals and said reference wave;

calculating means connected to said phase comparison means for computing the refractive-index profile of the test object from said phase differences, said source being a Zeeman-effect laser emitting a composite beam containing said first and second monochromatic beams, said optical means including the quarter-wave plate positioned for translumination by said composite beam and a polarizer inserted between said quarter-wave plate and said holder for separating rays of the first and second beams from each other;

another polarizer disposed in said field between said holder of said second photoelectric means for reconfining the rays of said first and second beams guided around and through the test object, said holder comprising a cell field with a transparent fluid whose refractive index matches a constant refractive index $n_c$ of a cladding of a workpiece of vitrious material constituting said test object and being used for the manufacture of an optical fiber and having a core whose refractive-index profile is to be determined; and a phase-shift compensator in said cell immersed in said fluid translumination by the rays of said second beam traversing the workpiece, said compensator having a known refractive-index profile, said calculating means being programmed to take said known profile into account.

10. An apparatus as defined in claim 9 wherein said optical means further includes a beam splitter disposed upstream of said polarizer for directing part of said composite beam onto said first photoelectric means.

11. An apparatus as defined in claim 9 wherein said optical means further includes a beam expander upstream of said polarizer broadening said second beam in said plane to a width exceeding the diameter of the test object, said first photoelectric means being juxtaposed with said second photoelectric means downstream of said holder for receiving rays of said second beam bypassing the test object together with rays of said first beam.

12. An apparatus as defined in claim 9 wherein said calculating means is programmed to compute the refractive-index profile of the core according to the relationship $$n(\rho) - n_c = -\frac{\lambda}{2\pi^2} \int_\rho^\infty \frac{d\phi}{dr} \cdot \frac{dr}{\sqrt{r^2 - \rho^2}}$$

where $\phi$ is the phase of a ray of said second beam transluminating said core at a distance $r > \rho$ from the axis, $n(\rho)$ is the refractive index of the core at distance $\rho$ from the axis, and $\lambda$ is the wavelength of said second beam.

13. An apparatus as defined in claim 9 wherein said compensator comprises a complementary hologram of a standard workpiece to be duplicated.

* * * * *